United States Patent [19]

Holtkamp

[11] Plant 4,302

[45] Sep. 19, 1978

[54] AFRICAN VIOLET PLANT

[75] Inventor: Reinhold Holtkamp, Isselburg, Fed. Rep. of Germany

[73] Assignee: Gesellschaftsvertrag uber die Erfindergemeinschaft "Optimara", Isselburg, Fed. Rep. of Germany

[21] Appl. No.: 743,150

[22] Filed: Nov. 18, 1976

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet plant having relatively large star-shaped flowers having a deep red flower color; shiny foliage; fast and vigorous growth; very strong and upright stems, and long blooming period.

1 Drawing Figure

1

The present invention comprises a new and distinct cultivar of African violet plant, botanically known as *Saintpaulia ionantha,* and hereinafter referred to by the cultivar name Pennsylvania.

Pennsylvania, referred to during the selection process by the designation b.265/3-73/76 red star is a product of a planned breeding program which had the objective of creating a new African violet cultivar with large red-purple, star-shaped flowers, normal to semi-double; upright strong flower stems, uniform bouquet, vigorous growth, and prolonged blooming period. These traits in combination were not present in previously available commercial cultivars of African violets.

The new cultivar was originated from a cross made in a controlled breeding program in Isselburg, Rhineland, Germany. The female, or seed parent was an unpatented cultivar identified by the breeding No. red XIX 2. The male, or pollen parent was an unpatented variety identified by the breeding No. FI pink 43-4.

The new cultivar Pennsylvania was selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany has demonstrated that the combination of characteristics as herein disclosed for the new cultivar are firmly fixed and are retained through successive generations of asexual reproduction.

The following observations, measurements and values describe plants grown in Isselburg, Rhineland, Germany under greenhouse conditions which closely approximate those generally used in commercial practice.

The following traits have been repeatedly observed and are determined to be basic characteristics of Pennsylvania which in combination distinguish this African violet as a new and distinct cultivar:

1. Relatively large, star-shaped flowers.
2. Red-purple flower color.
3. Shiny foliage color.
4. Fast and vigorous growth.
5. Very strong, upright stems.
6. Long blooming period.
7. Non-dropping flowers.

The accompanying photographic drawing shows a typical specimen plant of the new cultivar. The colors appearing in the photograph are as true as possible with color illustrations of this type.

2

In the following description, color references are made to the Munsel Limit Color Cascade Chart, except where general color terms of ordinary significance are employed, and except for the flower color values, which are based on R.H.S. Colour Chart, 1966 edition.

Botanical classification: *Saintpaulia ionantha,* Ramat. cv Pennsylvania.

Parentage:

*Male parent.*—FI pink — color 43-4.

*Female parent.*—XIX 2 red — color 45-13.

Propagation: The new cultivar holds its distinguishing characteristics through successive propagations by leaf cuttings and by division of shoots.

Plant: From 8 cm. to 12 cm. tall when grown in pots, and approximately 25–30 cm. in diameter when fully grown.

*Leaves.*—General Form — round to oval. Diameter — 6.5–8 cm. Texture — soft. Aspect — shiny and slightly hairy. Veins — upper, visible; under, strongly pronounced, reddish in color. Color (upperside) — 21–15 old leaves; 20–15 young leaves. Color (underside) — 18–20 old leaves; 41–15 young leaves. Petiole — brown-red on young leaves to green-reddish on old leaves.

*Flowers.*—Buds form — cup-shaped, 1–3 mm. when small, 8–10 mm. before opening, color brown-red. Sepals: Color — 5 sepals, color 45-13. Calyx — splits to star-shape. Aspect — hairy on outside. Peduncle — brown-red in color, strong upright 2–3 cm.

*Individual flowers.*—Size — 45–55 mm. in diameter, generally flat when fully opened. Color: Upperside — 71A-B. Underside — approximately 71B. Borne — Every flower stem has 5–8 flowers on short strong peduncles. Shape — 5–7 petals, star-shaped almost flat. Corolla — 5–7 petals, generally of the same size; a few flowers tend to semi-double with 1–3 smaller petals in the center. Arrangement — sympetalous, rotate and bilaterally symmetrical with smooth edges. Flowering time — opening slowly; from visible bud to flower in 4–6 weeks; in flower 4–7 weeks depending on light and temperature conditions.

*Reproductive organs.*—Stamens — 5–7 in number composed of 2 anther cells which give 10–14 anthers to each flower. Arrangement — basifixed. Filaments — 3–4 mm. long, color 25-3.

Styles — one 6–8 mm. long, color 43–14. Pollen color — 27-3.

*Root.*—Well developed root system, white when young, turning brownish color on older plants.

*Disease resistance.*—Good, as experienced to date.

General observations: The described permanent characteristics reside in all plants developed. The stem, which is strong, erect and flexible, supports approximately 5–8 flowers, when the plant is at full maturity. Flowers first appear 6 weeks after potting, with most of the flowers being single and few double with 1–3 smaller petals in the center. The new cultivar is particularly notable for the strong upright flower stems which support the large star-shaped flowers which have a red-purple flower color, and its attractive, evenly growing foliage which tends to spread radially outward from the flowers at the center of the plant, with the flowers being free above the foliage. The flower head itself contains from 5–8 blooms on each stem and nearly double that number at second blooming. The flowers do not drop from the stem after withering.

I claim:

1. A new and distinct cultivar of African violet known by the cultivar name Pennsylvania and particularly characterized as to novelty by the combined characteristics of relatively large star-shaped flowers having a red-purple flower color; shiny foliage; fast and vigorous growth; very strong and upright stems; long blooming period and non-dropping flowers.

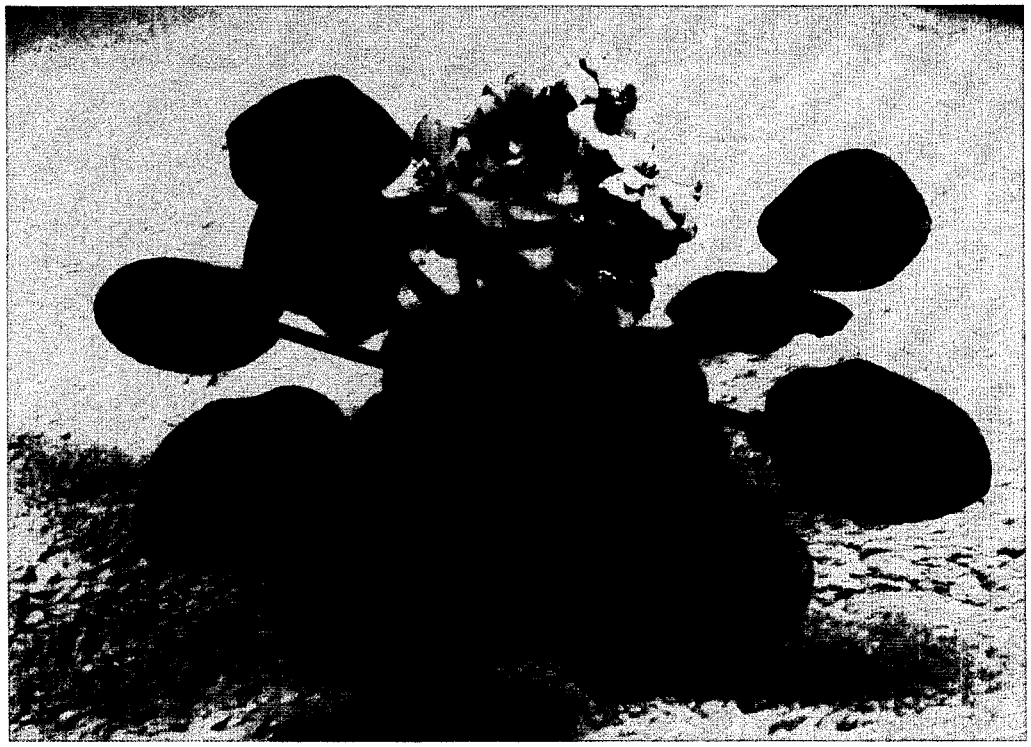

* * * * *